United States Patent
Burk

[11] Patent Number: 6,142,990
[45] Date of Patent: Nov. 7, 2000

[54] MEDICAL APPARATUS, ESPECIALLY FOR REDUCING INTRAOCULAR PRESSURE

[75] Inventor: Reinhard O. W. Burk, Heidelberg, Germany

[73] Assignee: Heidelberg Engineering Optische Messsysteme GmbH, Heidelberg, Germany

[21] Appl. No.: 09/023,214

[22] Filed: Feb. 13, 1998

[30] Foreign Application Priority Data

Feb. 15, 1997 [DE] Germany ............ 197 05 815

[51] Int. Cl.⁷ ............................................. A61B 17/36
[52] U.S. Cl. ........................... 606/6; 606/4; 606/17; 607/89
[58] Field of Search .................. 606/14, 15, 16, 606/17, 4, 5, 6; 607/89–90

[56] References Cited

U.S. PATENT DOCUMENTS

| | | |
|---|---|---|
| 5,123,902 | 6/1992 | Mueller et al. . |
| 5,222,952 | 6/1993 | Loertscher . |
| 5,292,320 | 3/1994 | Brown et al. ............ 606/15 |
| 5,370,641 | 12/1994 | O'Donnell, Jr. . |
| 5,431,646 | 7/1995 | Vassiliadis et al. . |
| 5,531,741 | 7/1996 | Barbacci ............... 606/15 |
| 5,575,787 | 11/1996 | Abela et al. ........... 606/11 |
| 5,688,264 | 11/1997 | Ren et al. ............. 606/15 |

FOREIGN PATENT DOCUMENTS

| | | |
|---|---|---|
| 38 31 141 | 3/1990 | Germany . |
| WO 92/17138 | 10/1992 | WIPO . |
| 95/34247 | 12/1995 | WIPO . |

*Primary Examiner*—Linda C. M. Dvorak
*Assistant Examiner*—S Harris-Ogugua
*Attorney, Agent, or Firm*—Evenson, McKeown, Edwards & Lenahan, P.L.L.C.

[57] ABSTRACT

A medical apparatus especially for lowering intraocular pressure by acting on the Schlemm's canal and on the tissue of the trabecular meshwork directly in contact with the Schlemm's canal, including a probe containing a photoconductor which is curved or elastically or plastically deformable to a curved configuration and which is connected to a laser, the photoconductor having a surface coating having at least one emission window therein facing the inner curvature of the photoconductor, the emission window permitting a laser beam to issue from the photoconductor at an angle of 90° to the curvature of the photoconductor.

20 Claims, 1 Drawing Sheet

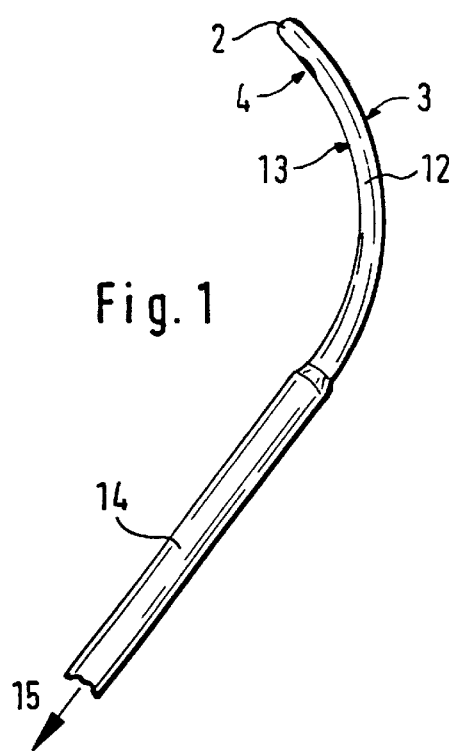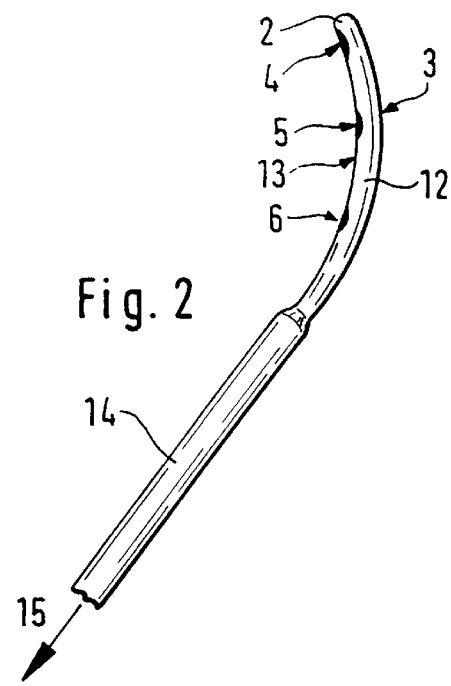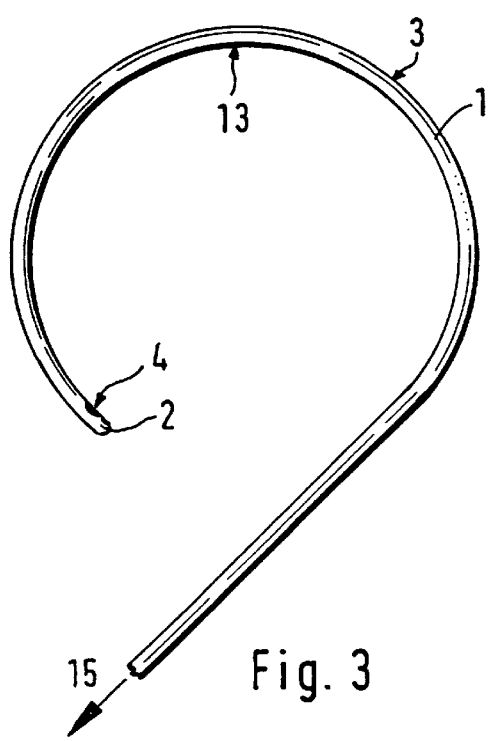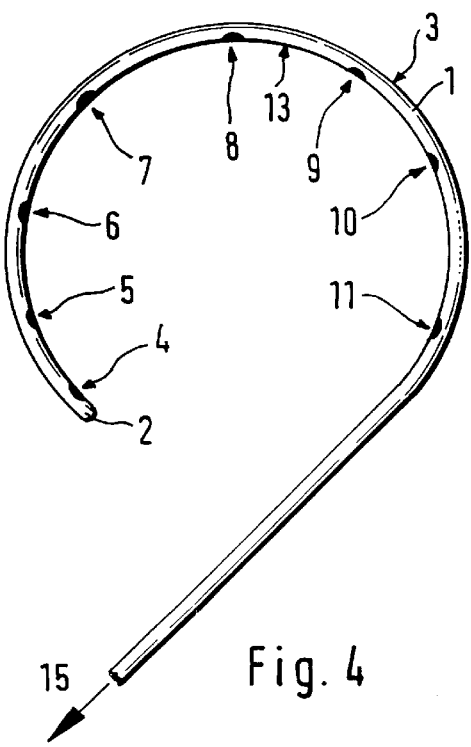

MEDICAL APPARATUS, ESPECIALLY FOR REDUCING INTRAOCULAR PRESSURE

BACKGROUND OF THE INVENTION

The invention relates to a medical apparatus for reducing intraocular pressure by acting upon the Schlemm's canal and the tissue of the trabecular network directly in contact with the Schlemm's canal, comprising a probe with a photoconductor connectable to a laser.

International Patent Application No. WO 92/17138 A2 discloses a medical apparatus of this type having a laser, to which a probe is connected by a photoconductor. The end of the photoconductor or fiber optic is disposed in a sleeve which is introduced into the probe housing, and inside the housing there are additional light conducting means such as lenses and prisms for adjusting and deflecting the beams. The apparatus and especially the probe are not easy to use in microsurgery due to their large size.

Moreover, a method and an apparatus for microsurgery on the eye by laser radiation are disclosed in published German Patent Application No. DE-OS 38 31 141. This apparatus includes a handpiece in which a fiber optic or photoconductor, on the one hand, and on the other an aspirating or flushing system for removing the tissue ablated by the laser beam, are provided. The light issues frontally from the free end of the photoconductor, the end of the photoconductor being disposed together with the aspirating or rinsing system in a special head piece. This apparatus too has appreciable dimensions which limit its use in microsurgery to special cases.

Glaucoma is one of the most frequent causes of blindness in the industrial countries. The common characteristic of this class of diseases in by far the greatest number of cases is an elevation of the intraocular pressure above a level tolerated by the optical nerve and nerve sheath. Untreated, a progressive atrophy of the optical nerve takes place. The progressive loss of nerve fibers results in the late stages of the disease in advancing losses of peripheral vision, and if untreated an irreversible, complete loss of function occurs, plus blindness. Treatment is based on the particular form of the glaucoma, the lowering of the intraocular pressure being the most prominent. The cause of the pressure increase is an elevated resistance in the aqueous humor drainage system. More than 80% of the aqueous humor, which is formed at a rate of approximately 2.5 $\mu$l/min, leaves the eye in the area of the corner of the anterior chamber, and more than 20% in the area of the ciliary body. Through the trabecular meshwork in the corner region of the chamber it reaches the Schlemm's canal and is carried through the aqueous humor veins under the conjunctiva, where resorption takes place in the vessels of the conjunctiva. The main resistance to drainage of the aqueous humor is in the inner wall of the Schlemm's canal and the adjacent trabecular meshwork. The treatment of glaucoma in the early stage of the disease is primarily with drugs. If sufficient pressure-reducing effect cannot be achieved, then surgical or laser surgery methods are employed. The methods heretofore available for intraocular pressure reduction other than by drug treatment are characterized by the fact that they do not act primarily at the locus of the most severe elevation of resistance.

Argon laser trabecular surgery is known, in which laser pulses are aimed through the anterior chamber at the trabecular meshwork via a contact glass with special lens systems on the slit lamp, which are intended to produce a stretching of the trabecular meshwork, and thus to improve the aqueous humor drainage into the Schlemm's canal. This procedure does result in a temporary reduction of intraocular pressure in most cases; however, due to the deflection of the laser beam by the anterior chamber onto the opposite side of the meshwork, the accuracy of aim is limited; the formation of adhesions (synechiae) in the area of the corner region of the chamber is one of the complications. In particular, it is difficult to control the depth of penetration of the laser pulses.

Also known is photoablation of the trabecular meshwork ab interno, in which either an erbium-Yag laser (Er:Yag) or a neodymium-Yag laser (Nd:Yag) or an excimer laser is used, whose pulses are aimed by means of fiber optics through the anterior chamber of the eye at the trabecular meshwork. Moreover, experiments have been undertaken to apply the laser pulses of an Nd:Yag laser through a contact glass at the opposite chamber corner region, without opening the eye. Alternately, ab interno sclerostomies also have been performed experimentally with pulsed dye lasers or argon lasers through a contact glass. Also in these methods it is difficult to control the depth of penetration of the laser pulses. Many experimenters are attempting a breakthrough effect through the adjacent sclera in order to open the subjunctival chamber (region directly under the pupil conjunctiva) and facilitate direct drainage in this region. Due to the scarring reactions these techniques have been unable to achieve any progress beyond a series of clinical experiments.

In the case of the known laser sclerostomy ab externo, a fistula for aqueous humor drainage under the conjunctiva has been created, in which after the ocular conjunctiva has been opened, the entire thickness of the sclera is penetrated. In this process an extensive defect is produced in the sclera. Any lasting resorption of the intraocular fluid requires that the access must not scar, but in this process it is a typical complication, the same as in the conventional operations performed manually. In contrast to the conventional surgical methods, however, the iris is not also partially removed (iridectomy) during laser sclerostomy, so that another possibility of complication is that the fistula may be closed by pulling in the iris. Attempts are often made to control the scarring from overshooting in the area of the conjunctiva through supplemental medication by antimetabolites, such as Mitomycin C or 5-fluorouracil. A serious disadvantage here is the toxicity of the substances used.

All of the experimentally tested medical devices and methods that are presently in clinical use have in common that they do not selectively achieve an improvement of the intraocular fluid drainage at the intraocular structures which are the locus of the main resistance in the system of drainage from the anterior chamber of the eye. In the known methods the laser pulse is aimed through the anterior chamber at the opposite tissue areas. In the known methods the first effects take place in the area of the trabecular meshwork, and the effects that likewise occur in the deeper structures cannot be evaluated.

SUMMARY OF THE INVENTION

It is the object of the invention to provide a medical apparatus which avoids the above disadvantage and which will be small and compact and yet be simple to operate.

Another object of the invention is to provide a medical apparatus which is to be used mainly in microsurgery and/or in ocular medicine.

It is also an object of the invention to provide a medical apparatus which can reduce the resistance to the drainage of the aqueous humor within the eye precisely at those structures which are responsible for the main component of the resistance to such drainage, while other ocular tissue components are protected.

These and other objects are achieved in accordance with the present invention by providing a medical apparatus for reducing intraocular pressure by acting upon the Schlemm's canal and the tissue of the trabecular network directly in contact with the Schlemm's canal, the apparatus comprising a probe comprising a photoconductor connectable to a laser, the photoconductor being provided with a surface coating having at least one emission window therein, and the at least one emission window being disposed in a curved or bendable section of the photoconductor.

The apparatus of the invention is characterized by a functional design and compact construction. It is suitable for use in microsurgery for the removal or alteration of tissues, and especially in ocular medicine for the reduction of intraocular pressure. In contrast to the known laser surgery equipment, the apparatus of the invention makes it possible to remove tissues in a sequence contrary to the direction of the drainage of a tissue fluid. Thus, by means of the apparatus of the invention, it is possible to perform a laser trabeculotomy of the Schlemm's canal (SKLT) with the aim of reducing resistance to intraocular drainage precisely at those structures which are responsible for the main component of such resistance. All other tissue components are to be spared insofar as possible. The medical apparatus enables intraocular pressure to be lowered by acting on the Schlemm's canal, and/or on the tissue directly deposited in the Schlemm's canal, by means of the photoconductor probe which has an arcuate and/or flexible section. By means of the apparatus of the invention, it is possible to produce pores in the tissue, especially in the trabecular meshwork, without detriment to adjacent tissue structures. This is quite generally the object in microsurgery and tissue manipulation.

In ophthalmology what is special in the method practiced according to the invention is seen in the fact that, in contrast to the laser surgery equipment which has long been tried and tested to date, the order in which the tissues are removed is contrary to the direction of flow of the aqueous humor. The aqueous humor leaves the eye by passing out of the anterior chamber through the trabecular meshwork and entering the Schlemm's canal through the inner wall of the latter, and, passing from there, it leaves the eye through the aqueous humor veins. In this identical order the tissue ablation is brought about by minimally invasive ab interno laser surgery techniques that have heretofore been tested. However, the depth of penetration is only poorly controlled, and an opening in the outer wall of the Schlemm's canal cannot be reliably assured. This has even been brought about deliberately by a number of working groups and the adjacent sclera has additionally been penetrated in order to achieve an additional drainage of aqueous humor. Laser trabeculotomy of the Schlemm's canal, on the other hand, has the purpose of leaving the Schlemm's canal as intact as possible, and to create only pores in the inner wall which is adjacent to the anterior chamber of the eye and is separated from it only by the trabecular meshwork. The structures to be treated in Schlemm canal laser trabeculotomy are the inner wall of the Schlemm's canal (the margin of the Schlemm's canal facing the anterior chamber) and the tissue of the juxtacanalicular (i.e., directly attached to the Schlemm's canal) trabecular meshwork. The laser treatment of the Schlemm's canal according to the invention is a combination of the known laser-induced tissue ablation from the area of the trabecular meshwork by the surgical access according to Harms and Mackensen.

BRIEF DESCRIPTION OF THE DRAWINGS

The invention will be described in further detail hereinafter with reference to illustrative preferred embodiments depicted in the accompanying drawings without limiting its scope. In the drawings:

FIG. 1 shows a first embodiment of the configuration of such an apparatus;

FIG. 2 shows an additional embodiment of the apparatus of FIG. 1;

FIG. 3 shows an apparatus with a photoconductor configured as a nearly closed circle; and FIG. 4 shows a configuration of the embodiment depicted in FIG. 3.

DETAILED DESCRIPTION OF PREFERRED EMBODIMENTS

With the apparatus according to the invention, after the surgical preparation of the access to the Schlemm's canal, instead of the conventional surgical trabeculotomy probe, with which only an imprecise and largely uncontrolled tearing open of the fabric structures can be performed, a flexible photoconductor which comprises an elastic and/or plastic material is introduced into the Schlemm's canal. The Schlemm's canal is an annular structure; the circular diameter of the Schlemm's canal is slightly greater than the thickness of the cornea of the particular patient being treated. For insertion into the Schlemm's canal of eyes having a horizontal corneal diameter of 10 to 12 mm, the photoconductor probe 12 is flexible toward the inside curve 13. The maximum probe diameter is about 400 $\mu$m, preferably 320 $\mu$m, so as to be able to be inserted atraumatically into a normal Schlemm's canal. Since a few eyes have a Schlemm's canal diameter of only 200 $\mu$m, smaller photoconductor diameters may also come into use. In the embodiment shown in FIGS. 1 and 2, the photoconductor 12 extends over an arc of about 90° to 120° to the right and left for insertion from the right or left into the Schlemm's canal. The curvature or bending radius is on the order of a few millimeters and is especially greater than 4 mm, preferably greater than 5 mm; the said radius amounts to a maximum of 7 mm, preferably 6 mm. The photoconductor's tip 2 is rounded according to the invention.

The probe has a surface coating 3 which provides for the exit of the laser beam at an emission window 4 (FIG. 1) near the tip 2 of the probe, or at a plurality of emission windows 4 to 6 (FIG. 2), at an angle of 90° toward the inside curve 13 of the flexible photoconductor 12. A color coating absorbing the corresponding wavelength, or a mirror coating or other kinds of shielding, e.g.,made of carbon material or plastic, is used as the surface coating 3. The arcuate section of the photoconductor 12 adjoins a handle 14 in which the photoconductor 12 is embedded. The handle 14 can also extend out from the curvature defined by the probe at an angle of about 90°. The photoconductor has a laser terminal 15. According to the invention, at its end forming the probe, the photoconductor is made at least partially flexible and is provided with the surface coating 3 that is impermeable to light or laser beams. This surface coating 3 has at least one emission window through which the light or laser beams can issue laterally from the photoconductor. The photoconductor connected to the laser can be elastically and/or plastically shaped to an arcuate section. Even if the flexible and/or bendable and/or bent section of the section provided with the surface coating forms approximately an arc, still other curve shapes can be achieved, such as a parabola, ellipse or the like, can be defined or achieved in order to provide optimum conditions for a particular use of the medical apparatus of the invention. Independently of the particular concrete configuration of the bend, the at least one emission window lies preferably near the inside of the said section. According to the invention, the flexible and/or bendable and/or bent section is adjoined by the handle 14 through which the photoconductor 12 extends. The other end of the photoconductor 12 is connected to the above-mentioned laser terminal. The tip 2 is preferably provided with the surface coating essential to the invention, so that no laser light can issue lengthwise from the photoconductor.

This probe can be connected to a conventional commercial Er:Yag laser. At an energy of 4 mJ, it is possible with a pulse duration of 100 microseconds, 150 microseconds and 250 microseconds to produce tissue ablations in the trabecular meshwork with pore sizes of approximately 100 $\mu$m, 120 $\mu$m and 200 $\mu$m, respectively. The thermal effects in the margins of the pores are of a magnitude of up to 10 $\mu$m, 20 $\mu$m and as much as 60 $\mu$m. To achieve a number of pores within the inner wall of the Schlemm's canal, the probe 12 is inserted into the canal.

In the embodiments shown in FIGS. 3 and 4, the photoconductor 1 is in a virtually full circular form and can thus cover the entire Schlemm's canal. According to FIG. 3, an emission window 4 is located near the tip 2 of the probe.

In addition to the single laser beam emission window 4 near the tip of the photoconductor 2, a plurality of emission windows 5 to 11 can be opened simultaneously on the inner radius of the photoconductor (FIG. 4), at an angular spacing of, for example, 100°, 60° or 40°, for three, five or eight simultaneous laser pulses, for example.

A holmium laser or an Nd:YLF picosecond laser system can be used as the laser source. When an Nd:YLF laser system is used, the energy required for tissue ablation can be further reduced. It is possible to use a two-stage system which consists of a diode-pumped actively modem-coupled oscillator and a regenerative amplifier. The pulses produced in the oscillator at a wavelength of 1053 nm have a duration of about 25 ps at a pulse energy of 0.2 nJ. These pulses are coupled into the regenerative amplifier through a polarization circuit and amplified therein up to a pulse energy of 1.5 mJ. At pulse durations of about 30 ps the process of tissue ablation begins at energy densities of 20 J/cm$^2$. These low energies permit a virtually local tissue removal with minimal damaging effect on surrounding structures.

Furthermore, it is readily possible to use a commercially available diode laser system in connection with the described method and apparatus, especially when a coagulation effect is desired due to special anatomical circumstances. The term for this variant of SKLT is laser trabeculocoagulation of the Schlemm's canal.

The tissue ablation takes place contrary to the direction of the aqueous humor drainage. This assures that only the regions of the greatest resistance in the aqueous humor drainage system are treated.

The method of laser trabeculotomy of the Schlemm's canal has been designed with the following criteria:

The introduction of the photoconducting fiber into the Schlemm's canal achieves the following principal effects:

(1) The tissue-removing laser beam is aimed directly against the inner wall of the Schlemm's canal and thus is in the immediate vicinity of the structure to be treated. It is assured that the inner wall of the Schlemm's canal is treated and also the adjacent (juxtacanalicular) trabecular meshwork can be operated on by laser surgery.

(2) The outside radius of the photoconductor extends along the outer wall of the Schlemm's canal, and this wall structure is thus simultaneously protected mechanically against undesired effects.

This procedure makes it possible to produce pores in the trabecular meshwork without damage to adjacent structures.

In contrast to the method described herein, it has been common practice heretofore to aim the laser pulse through the anterior chamber against tissue areas lying opposite. In the previously known methods, the first effects are produced in the area of the trabecular meshwork, and the effects that also occur in deeper structures cannot be estimated.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A medical apparatus for reducing intraocular pressure by acting upon a Schlemm's canal and tissue of a trabecular network directly in contact with the Schlemm's canal, said apparatus comprising:

a probe, insertable into the Schlemm's canal so that an outer radius thereof extends along an outer wall of the Schlemm's canal, comprising a photoconductor connectable to a laser, and a surface coating having at least one emission window therein provided on said photoconductor, said probe photoconductor and surface coating having a combined diameter of at most about 400 $\mu$m, said at least one emission window being disposed in a curved or bendable section of the photoconductor so that laser light issues directly toward an interior wall of the Schlemm's canal to perforate the interior wall and the trabecular network while remaining areas of the Schlemm's canal and the trabecular network are protected from the laser light by said surface coating, wherein the tissues of the interior wall and the trabecular network are removed in a sequence contrary to a drainage direction of fluid.

2. An apparatus according to claim 1, wherein said at least one emission window is disposed adjacent the end of the photoconductor.

3. An apparatus according to claim 1, wherein said at least one emission window permits laser light to issue laterally from the photoconductor.

4. An apparatus according to claim 1, wherein said at least one emission window permits laser light to issue through a radially inner curved surface of the photoconductor.

5. An apparatus according to claim 1, wherein said at least one emission window permits laser light to issue from a curved section of the photoconductor at an angle of substantially 90° to a tangent to said curved section of the photoconductor.

6. An apparatus according to claim 1, wherein said at least one emission window is disposed on a radially inner side of said curved or bendable section of the photoconductor.

7. An apparatus according to claim 1, wherein the photoconductor and the surface coating are flexible or elastically or plastically deformable.

8. An apparatus according to claim 1, wherein the photoconductor comprises a curved portion extending over an angle of from about 90° to about 120°.

9. An apparatus according to claim 8, wherein said curved portion has a circular curvature.

10. An apparatus according to claim 8, wherein said curved portion has a right-handed curvature.

11. An apparatus according to claim 8, wherein said curved portion has a left-handed curvature.

12. An apparatus according to claim 1, wherein said photoconductor extends over the entire length of the Schlemm's canal of an eye treated with said apparatus.

13. An apparatus according to claim 1, wherein the photoconductor has a rounded tip.

14. An apparatus according to claim 13, wherein the photoconductor is provided with a handle spaced a distance from the photoconductor tip, and the photoconductor is extended through said handle to a laser terminal.

15. An apparatus according to claim 1, wherein the photoconductor coating has a plurality of emission windows therein facing an inner curvature of the photoconductor through which laser pulses issue simultaneously.

16. An apparatus according to claim 1, wherein said photoconductor is connected to a laser selected from the group consisting of Er:Yag lasers, holmium lasers, Nd:YLF lasers and diode lasers.

17. An apparatus according to claim 1, wherein the probe photoconductor and surface coating have a combined diameter of at most about 320 $\mu$m.

18. An apparatus according to claim 1, wherein the probe has a curved portion containing said at least one emission window, said curved portion having a radius of curvature in the range from about 4 mm to about 7 mm.

19. An apparatus according to claim 18, wherein said curved portion has a radius of curvature on the order of at least about 5 mm.

20. An apparatus according to claim 18, wherein said curved portion has a radius of curvature of at most about 6 mm.

* * * * *